(12) United States Patent
Bhaskaran et al.

(10) Patent No.: US 9,737,495 B2
(45) Date of Patent: Aug. 22, 2017

(54) PROCESS FOR OBTAINING PURIFIED PTEROSTILBENE AND METHODS OF USE THEREOF

(75) Inventors: Sunil Bhaskaran, Maharashtra (IN); Mohan Vishwaraman, Maharashtra (IN)

(73) Assignee: Indus Biotech Private Limited, Pune (IN)

( * ) Notice: Subject to any disclaimer, the term of this patent is extended or adjusted under 35 U.S.C. 154(b) by 0 days.

(21) Appl. No.: 13/059,042

(22) PCT Filed: Jul. 30, 2009

(86) PCT No.: PCT/IN2009/000435
§ 371 (c)(1),
(2), (4) Date: Feb. 14, 2011

(87) PCT Pub. No.: WO2010/150271
PCT Pub. Date: Dec. 29, 2010

(65) Prior Publication Data
US 2011/0144053 A1  Jun. 16, 2011

(30) Foreign Application Priority Data
Jun. 22, 2009 (IN) ................ 01481/MUM/2009

(51) Int. Cl.
C07C 39/215 (2006.01)
A61K 31/05 (2006.01)
A61K 31/09 (2006.01)
C07B 63/00 (2006.01)
C07C 41/36 (2006.01)

(52) U.S. Cl.
CPC ............. *A61K 31/09* (2013.01); *C07B 63/00* (2013.01); *C07C 41/36* (2013.01)

(58) Field of Classification Search
CPC ...... C07C 39/215; A61K 31/05; A61K 31/724
USPC ................................ 536/103; 562/51; 514/58
See application file for complete search history.

(56) References Cited

U.S. PATENT DOCUMENTS

| 2009/0069444 A1* | 3/2009 | Joseph et al. ............ 514/719 |
| 2009/0163580 A1* | 6/2009 | Yatcilla ................ A61K 31/05 514/456 |
| 2009/0175803 A1* | 7/2009 | Rubin et al. ............. 424/48 |

FOREIGN PATENT DOCUMENTS

WO   WO 2009/032870 A2   3/2009

OTHER PUBLICATIONS

Pari et al., "Effect of Pterostilbene on Hepatic Key Enzymes of Glucose Metabolism in Streptozotocin- and Nicotinamide-Induced Diabetic," *Life Sci.* (2006), 79(7):641-645.

\* cited by examiner

*Primary Examiner* — Shaojia Anna Jiang
*Assistant Examiner* — Everett White
(74) *Attorney, Agent, or Firm* — DLA Piper LLP (US)

(57) ABSTRACT

The present invention relates to a process of extraction and purification of a stilbenoid, pterostilbene, from botanical sources. The process involves obtaining pterostilbene having high degree of purity and the present invention also relates to pure form of pterostilbene obtained. The invention also relates to complexing the pterostilbene with carriers such as cyclodextrin for improving its water solubility and bioavailability. The present invention also describes a process for inhibition of Histone Deacetylases using pterostilbene optionally along with a carrier, and a method of managing Poly Glutamine repeat disorders by the administration of pterostilbene optionally along with a carrier.

15 Claims, 3 Drawing Sheets

PROCESS FOR OBTAINING PURIFIED PTEROSTILBENE AND METHODS OF USE THEREOF

CROSS REFERENCE TO RELATED APPLICATIONS

This application is a 35 USC §371 National Stage application of International Application No. PCT/IN2009/000435 filed Jul. 30, 2009, now pending; which claims the benefit under 35 USC §119(a) to India Patent Application No. 01481/MUM/2009 filed Jun. 22, 2009. The disclosure of each of the prior applications is considered part of and is incorporated by reference in the disclosure of this application.

TECHNICAL FIELD

The present invention relates to a method of extraction and purification of a stilbenoid, pterostilbene, from botanical sources. The process involves obtaining pterostilbene having high degree of purity and the present invention also relates to pure form of pterostilbene obtained. The invention also relates to complexing the pterostilbene with carriers such as cyclodextrin for improving its water solubility and bioavailability. The present invention also describes a process for inhibition of Histone Deacetylases using pterostilbene, along with a method of managing Poly Glutamine repeat disorder through administration of pterostilbene.

BACKGROUND AND PRIOR ART OF THE INVENTION

Huntington's disease (HD) is a progressive, inherited, degenerative brain disorder that produces physical, mental and emotional abnormalities in the body. This disease was earlier referred to as Huntington's Chorea, derived from the Greek word 'choreography', or dance. The name refers to the involuntary, jerky movements which develop in later stages of this disease. This disease is classified as a 'rare disease' by the Office of Rare Diseases (ORD) which is a part of the National Institute of Health (NIH), USA. This disease affects men and women indifferently and occurs in adults at variable ages.

HD is a hereditary, neurodegenerative disorder of the CNS which affects the basal ganglia of the brain. The basal ganglia are the part of the brain which controls actions of speech, movement and thought. This disease is transmitted as an autosomal dominant trait with its penetration increasing with age. The gene mutation occurs in an expansion of repeated trinucleotide sequences in the genetic make up. The genetic defect responsible for HD is a small sequence of DNA on chromosome 4 in which several base pairs are repeated many times. The normal gene has three DNA bases, composed of the sequence CAG which codes for the amino acid glutamine. In people with HD, the sequence abnormally repeats itself dozens of times, causing multiple glutamine repeats leading to a polyglutainine repeat condition. Over time, and with each successive generation, the number of CAG repeats may expand further.

HD occurs in 3 major and relatively distinct stages based on the severity of the disease: early, middle and late. In all stages of HD, weight loss is an important complication that can correspond to worsening symptoms and should be countered by adjusting the diet and maintaining appetite. On a behavioral level, this disease manifests as irritability, obsessions, compulsions, hallucinations, impaired memory, dementia and decreased ability to execute functions. Due to the location of the brain affected, these cognitive abnormalities are accompanied by motor abnormalities and impairment leading to (depending on the stage of the disease) disability in movement and coordination. Patients with early-stage Huntington disease have recently been shown to have reduced levels of branched chain amino acids (BCAA) which indicate an energy deficit with consequences reaching beyond the CNS. This energy deficit aspect which is seen in HD patients forms the basis of animal models used for the evaluation of potential drugs for HD.

Histone Deacetylyases (HDAC)

HDACs are enzymes that affect the acetylation status of histones and other important cellular proteins. The role of protein acetylation is an important post-translational modification that regulates cellular functions, including chromatin remodelling, transcriptional regulation, microtubular dynamics, intracellular transport, metabolism, and ageing. Levels of acetylation are controlled by histone acetylases (HATs) and HDACs which add or remove (respectively) acetyl groups from substrates. An increased acetylation (HAT activity) loosens the chromatin configuration leading to an increase in gene expression, while deacetylation (HDAC activity) condenses the chromatin leading to decreased gene expression and thus translation. Thus up-regulation of transcription can be achieved by the stimulation of HAT or the inhibition of HDAC.

HDAC Inhibitors and Polyglutamine-Repeat Disorders

HD is a polyglutamine-repeat disease and HDAC inhibitors have the potential to play an important therapeutic role in such diseases. The mechanism of neurodenegeration in certain polyglutamine-repeat diseases like HD are relatively well understood and is largely attributed to specific aspects of an aberration in neuronal homeostasis. This aberration is attributed to abnormal histone acetylation leading to a different chromatin remodelling thus leading to aberrant protein expression and interaction. Additionally the neuroprotective effect of HDAC inhibitors has been well documented in both invertebrate and mouse models for HD and other polyglutamine-repeat diseases.

Another aspect leading to the progression of HD is a defect in the microtubule-based transport which contributes to neuronal toxicity. In view of this, HDAC inhibition can compensate for the transport deficit by increasing α-tubulin acetylation. The HDAC responsible for the deacetylation of α-tubulin is the Class III HDAC called Sirtuins.

Sirtuins

Class III deacetylases or Sirtuins are named after "silent information regulator 2 (Sir2)" gene and are structurally different from other HDACs. There are 7 different kinds of sirtuins which have been identified and characterised and the main deacetylation activity is attributed to SIRT1, SIRT2, SIRT3 and SIRT5.

SIRT2 is a cystolic protein that deacetylates α-tubulin and microtubules and in specific is associated with the CNS since it has been shown to be localized to myelin sheaths and is implicated in the regulation of axonal myelination.

SIRT2 is responsible for the deacetylation of α-tubulin and the progression of HD is affected by the acetylated state of α-tubulin, an inhibition of SIRT2 can prove to be therapeutically effective in the treatment of HD.

An additional feature of HDAC inhibitors is that they are effective over a spectrum of diseases, mainly Polyglutamine-Repeat Diseases. Also HDAC inhibitors have improved selectivity, decreased toxicity, and have emerged as important drug targets.

Pterostilbene

Pterostilbene is a stilbenoid and is found in wine, peanuts, grapes, berries and certain species of *Pterocarpous*. Pterostilbene is one of the many aromatic hydrocarbons called 'stilbenes'. This compound has potent anti-diabetic properties, chemoprotective properties and is also being investigated for its anti-cancer properties.

Animal Models for the Evaluation of Hd: 3-NP Model

A variety of methods are available to evaluate and/or monitor Huntington's disease. A variety of clinical symptoms and indicia for the disease are known. Based on the symptoms exhibited in HD, several animal models exist to evaluate potential drug candidates for this disease.

3-NP (Nitropropionic Acid) is known to cause symptoms of HD in rats. 3-NP is an inhibitor of mitochondrial respiration which on oxidation forms a covalent adduct with a catalytic-base arginine. Administration of 3-nitropropionic acid, an inhibitor of the mitochondrial citric acid cycle, produces a very selective striatal degeneration and results in a progressive locomotor deterioration in rodents resembling that of Huntington's disease.

US Pat. Pub. No.: S 2009/0069444 A1

This patent application refers to a composition which is used to treat oxidative stress and thereby renders an improvement in working memory of a subject when administered between dosage ranges of 2.5-20 mg/kg of body weight.

To establish the effect of the composition of the improvement of learning and memory this application uses the Morris Water Maze example. This is a method to test the spatial learning a memory of a subject and this test is dependant on the age and diet of the subject. This example concluded the effects of the diet containing Pterostilbene on cognitive performance and working memory. Further this example claims the use of Pterostilbene in the treatment of oxidative stress thereby improving cognitive function.

However there is no mention or indication of the use of Pterostilbene for the improvement of factors related to specific disorders of the CNS. It is important to note that although disorders of the CNS are age related, they cannot merely be attributed to oxidative stress. There can be a multitude of other factors mainly genetic and enzymatic ones which are involved and thus lead to the onset or progression of CNS diseases.

US Pat. Pub. No.: US 2007/0249647 A1

This patent application deals with the use of substituted cis or trans stilbenes for the treatment of cancer, pre-cancer conditions, inflammatory conditions and ischemic injuries like stroke. The primary method of action of the claimed composition of this patent application is by the inhibition of NF-κB activity. Based on this inhibition this application claims the use of the composition in diseases like diabetes and Alzheimer's.

SUMMARY OF THE INVENTION

Accordingly, the present invention relates to a process of obtaining Pterostilbene of about 50% to about 99% purity from botanical source, said process comprising steps of (a) pulverizing and extracting of plant material with aqueous alcohol to obtain an extract, (b) filtering the extract and subjecting it to chromatography followed by elution with aqueous alcohol, (c) concentrating the eluted solvent of step (b) to obtain a paste, followed by redissolving the paste in aromatic solvent to obtain a solution, and (d) column adsorption of the solution to obtain a semi-solid mass followed by drying to obtain the pterostilbene; purified pterostilbene having purity of about 50% to about 99% complexed with cyclodextrin, optionally along with pharmaceutical excipients; a process for inhibition of Histone Deacetylases using pterostilbene complexed with cyclodextrin, said process comprising step of contacting the histone deacetylase with pterostilbene; and a method of managing Poly Glutamine repeat disorder, said method comprising step of administering therapeutically effective amount of pterostilbene complexed with cyclodextrin, optionally along with pharmaceutical excipients, to a subject in need thereof.

DETAILED DESCRIPTION OF THE INVENTION

The present invention relates to a process of obtaining Pterostilbene of about 50% to about 99% purity from botanical source, said process comprising steps of
 a. pulverizing and extracting of botanical source with aqueous alcohol to obtain an extract;
 b. filtering the extract and subjecting it to chromatography followed by elution with aqueous alcohol,
 c. concentrating the eluted solvent of step (b) to obtain a paste, followed by redissolving the paste in aromatic solvent to obtain a solution; and
 d. column adsorption of the solution to obtain a semi-solid mass followed by drying to obtain the pterostilbene.

In another embodiment of the present invention, the botanical source is selected from a group comprising genus *Pterocarpus, Anogeissus* and *Vaccinium* or family Vitaceae.

In yet another embodiment of the present invention, the pulverizing is conducted to a mesh size of about 40 mesh to about 60 mesh to get pulverized material.

In still another embodiment of the present invention, the pulverized material is extracted at a temperature range of about 50° C. to about 60° C. for a duration of about 8 to about 12 hrs to get an extract, preferably 50° C. for 10 hrs.

In still another embodiment of the present invention, the extract is filtered through a clean stainless steel mesh or a clean cloth.

In still another embodiment of the present invention, wherein the aqueous alcohol is selected from a group comprising methyl alcohol, ethyl alcohol, propyl alcohol and butyl alcohol or any isomeric form thereof.

In still another embodiment of the present invention, the chromatography is Column Chromatography.

In still another embodiment of the present invention, the column is a polymeric adsorbent column.

In still another embodiment of the present invention, the eluted solvent is concentrated at a temperature range of about 40° C. to about 60° C. under vacuum, preferably 40° C.

In still another embodiment of the present invention, the aromatic solvent is selected from a group comprising benzene, toluene and xylene or any homolog thereof.

In still another embodiment of the present invention, the column used in column adsorption is Neutral Alumina column.

In still another embodiment of the present invention, the pterostilbene is in the form of free flowing powder.

In still another embodiment of the present invention, the preferred purity ranges from about 80% to about 99%.

In still another embodiment of the present invention, the process further comprising of complexing pterostilbene with a carrier.

In still another embodiment of the present invention, the carrier is cyclodextrin.

In still another embodiment of the present invention, the cyclodextrin is selected from a group comprising α-cyclodextrin, β-cyclodextrin or γ-cyclodextrin, preferably β-cyclodextrin.

The present invention relates to purified pterostilbene having purity of about 50% to about 99% complexed with cyclodextrin, optionally along with pharmaceutical excipients.

In an embodiment of the present invention, the cyclodextrin is selected from a group comprising α-cyclodextrin, β-cyclodextrin or γ-cyclodextrin, preferably β-cyclodextrin.

The present invention relates to a process for inhibition of Histone Deacetylases using Pterostilbene complexed with cyclodextrin, said process comprising step of contacting the histone deacetylase with pterostilbene.

In another embodiment of the present invention, the Histone Deacetylase is either SIRT1 or SIRT2.

In yet another embodiment of the present invention, the pterostilbene acts as an inhibitor of Histone Deacetylases.

In still another embodiment of the present invention, the cyclodextrin is selected from a group comprising α-cyclodextrin, β-cyclodextrin or γ-cyclodextrin, preferably β-cyclodextrin.

The present invention relates to a method of managing Poly Glutamine repeat disorder, said method comprising step of administering therapeutically effective amount of Pterostilbene complexed with cyclodextrin, optionally along with pharmaceutical excipients, to a subject in need thereof.

In another embodiment of the present invention, the Poly Glutamine Repeat disorder is Huntington's disease.

In yet another embodiment of the present invention, the Poly Glutamine repeat disorder comprises Spinocerebellar ataxias (SCAs) 1, Spinocerebellar ataxias (SCAs) 2, Spinocerebellar ataxias (SCAs) 3, Spinocerebellar ataxias (SCAs) 6, Spinocerebellar ataxias (SCAs) 7, Spinocerebellar ataxias (SCAs) 17, Spinal and bulbar muscular atrophy (SBMA) and Dentatorubropallidoluysian atrophy (DRPLA).

In still another embodiment of the present invention, the pterostilbene acts as an inhibitor of Histone Deacetylases for managing Poly Glutamine repeat disorder.

In still another embodiment of the present invention, the Histone Deacetylase is either SIRT1 or SIRT2, preferably SIRT2.

In still another embodiment of the present invention, the cyclodextrin is selected from a group comprising α-cyclodextrin, β-cyclodextrin or γ-cyclodextrin, preferably β-cyclodextrin.

In still another embodiment of the present invention, the therapeutically effective amount of pterostilbene ranges from about 2 mg/kg to about 20 mg/kg body weight of the subject.

In still another embodiment of the present invention, the subject is animal or human.

The present invention relates to the use of Pterostilbene for the treatment and/or management of neurodegenerative disorders. One embodiment of the present invention also relates to the extraction of Pterostilbene from botanical sources. Another embodiment of this invention refers to preparation of bioavailable pterostilbene with complexation with cyclodexdrin. Another embodiment of the present invention is obtaining Pterostilbene from botanical sources with a purity of about 50% to about 99%. In one embodiment of the present invention Pterostilbene is extracted from botanical sources of the species *Pterocarpus, Anogeissus* and fresh fruits of *vitis* and other berries.

In one embodiment of the process of extraction of Pterostilbene from botanical sources, the process comprises the following steps:

1. Based on the botanical source used:
   a. Chips of 10 mm 10 mm length were used for extraction and were pulverized in a hammer mill to a mesh size of 40 mesh to 60 mesh. The pulverized material was then loaded onto a vertical extractor; or
   b. Fruits and berries used for the extraction were from farm origin or frozen and pulped and were then loaded to be extracted.
2. A hot mixture of aqueous alcohol (ranging from 60% aliphatic protic alcohol to 10% by volume) was circulated in the extractor at 50 to 60° C. for 8 to 12 hrs to achieve maximum extractable in the liquid. The aliphatic protic alcohol used comprised methyl, ethyl, propyl, butyl, alcohol and/or their isomeric forms.
3. The clear extract of the above step was filtered through a clean stainless steel mesh or cloth to get clear liquid which was cooled to room temperature to remove the resinous material which falls out on cooling.
4. This clear liquid was passed through an adsorbent column comprising of Dowex-L-493 DOW CHEMICALS or its equivalent Amberlite XAD-4 manufactured by ROHM-HAAS.
5. The column outlet was monitored for the absence of the drug using Thin Layer Chromatographic techniques with a mobile phase of petroleum ether and ethyl acetate in the ratio of 7:3 on a pre-coated silica gel plate.
6. After complete exhaustion of the column, the column was washed clear of adhering impurities and colored matter with the solvent comprising of aqueous alcohol (percentage of aliphatic protic alcohols ranging from 60% to 10% by volume).
7. The column was eluted with the same alcohol which was used for adsorption cycle and washing cycle but the purity of the alcohol was ensured above 99%.
8. The completion of the elution was monitored by the Thin Layer Chromatographic technique which was used for absorption cycle.
9. The eluted solvent along with the compound was concentrated in a rotary evaporator under vacuum at 40° C. to 60° C. to get a paste. Alternatively it can directly be diluted with water in a suitable manner for further work-up.
10. The paste was then dissolved in a solvent mixture of aqueous alcohol where the alcohol was an aliphatic protic one comprising of either a combination or individually of ethyl, methyl, propyl, or butyl alcohol in the ratio of 1:1 and counter currently extracted with an aromatic solvent comprising of benzene and or its homologues preferably an aromatic solvent like toluene or xylene.
11. The extracted solvent was washed with water to remove colors and passed through a column comprising of Neutral alumina (aluminum oxide powder of 40 to 100 mesh size. The column was monitored by the Thin Layer Chromatographic technique and pure fractions were collected and concentrated to get a semi-solid mass.
12. The semisolid mass was dried under vacuum at 60 to 80° C. to get a free flowing powder. The above mentioned powder was analyzed for trans Pterostilbene content using HPLC.

13. The isolated pterostilbene powder was subjected to HPLC Analysis as mentioned below:
Column: Kromasil C-18 RP, 5μ 250 mm×4.6 mm
Detector: 313 nm UV
Flow rate: 1 ml/min
Mobile phase: A mixture of 0.1% Orthophosphoric acid in water:Acetonitrile mixed, filtered, degassed
Reference standard: Chromadex part no #16995-10, lot no16995-102 purity reagent 99.9%.

The isolated pterostilbene is obtained with high levels of purity, and this purity is obtained due to combination of various solvents and resin columns used in the process. The sequence of the entire process is also a critical factor which contributes towards the high levels of pure pterostilbene obtained.

The purity of the isolated pterostilbene ranges from about 50% to about 99%, preferably from about 60% to about 99%, more preferably from about 80% to about 99% and most preferably from about 92% to about 99%.

The isolated pterostilbene is optionally complexed with suitable carriers to make the compound more water soluble and bioavailable. The suitable carriers include various forms of cyclodextrin, selected from group comprising α-cyclodextrin, β-cyclodextrin or γ-cyclodextrin, preferably β-cyclodextrin.

The present invention is further elaborated with the help of accompanying examples and figures. However, the examples should not be construed to limit the scope of the invention.

Example 1

100 kg of *Pterocarpus marsupium* hardwood was cut in to small pieces of 10 mm in length. These pieces were pulverized to 40 mesh powder in a hammer mill and stacked in a vertical tubular extractor. The bottom of the extractor comprises of a perforated plate on which filtration cloth was fixed. The bottom of the extractor was connected to a receiver which in turn can be used as a reservoir for pumping the extract as well as circulation of the extract in the tube in counter current or concurrent manner.

The above mentioned mass was extracted with six bed volumes of 60% volume by volume, ethyl alcohol (aqueous) at 55° C. The bed was re-extracted in manner with an extract collected at the bottom and re-circulated in hot condition for 8 hrs and after 8 hrs it was filtered clear. The clear filtrate was passed from bottom of an adsorbent column comprising of Dowex L-493 and the liquid out flow was monitored by thin layer chromatography using a mobile phase of petroleum ether:ethyl acetate in the ratio of 7:3. After achieving column saturation the column was washed with 60% ethyl alcohol in water until no color.

The bed was eluted with pure ethyl alcohol at room temperature and the elutes were collected at the bottom. The eluted solvent was diluted with water to get the product in solution form in a 50% alcoholic solution. This was extracted with Toluene 50 liters X3 Times and the top toluene layer collected and Passed through 10 kg of Neutral alumina column and concentrated at 60° C. under vacuum. The resultant powder was analyzed by HPLC and was found to be 96% pure.

Example 2

100 kg of *Pterocarpus marsupium* hardwood was cut in to small pieces of 10 mm in length. These pieces were pulverized to 40 mesh powder in a hammer mill and stacked in a vertical tubular extractor. The bottom of the extractor comprises of a perforated plate on which filtration cloth was fixed. The bottom of the extractor was connected to a receiver which in turn can be used as a reservoir for pumping the extract as well as circulation of the extract in the tube in counter current or concurrent manner.

The above mentioned mass was extracted with six bed volumes of 60% volume by volume Isopropyl alcohol (aqueous) at 55° C. The bed was re extracted in manner with an extract collected at the bottom and re-circulated in hot condition for 8 hrs and after 8 hrs it was filtered clear. The clear filtrate was passed from bottom of an adsorbent column comprising of Amberlite XAD-4 and the liquid out flow was monitored by thin layer chromatography using a mobile phase of petroleum ether:ethyl acetate in the ratio of 7:3. After achieving column saturation the column was washed with 60% isopropyl in water until no color.

The bed was eluted with pure ethyl alcohol at room temperature and the elutes were collected at the bottom. The eluted solvent was diluted with water to get the product in solution form in a 50% alcoholic solution. This was extracted with 50 litersX 3 times Toluene and the top toluene layer collected and Passed through 10 kg of Neutral alumina column and concentrated at 60° C. under vacuum. The resultant powder was analyzed by HPLC and was found to be 99% pure.

Example 3

100 kg of *Anogeissus acuminata* (fassi) wood chips were cut in to small pieces of 10 mm in length. These pieces were pulverized to 40 mesh powder in a hammer mill and stacked in a vertical tubular extractor. The bottom of the extractor comprises of a perforated plate on which filtration cloth was fixed. The bottom of the extractor was connected to a receiver which in turn can be used as a reservoir for pumping the extract as well as circulation of the extract in the tube in counter current or concurrent manner.

The above mentioned mass was extracted with six bed volumes 60% volume by volume methyl alcohol (aqueous) at 55° C. The bed was re extracted in manner with an extract collected at the bottom and re-circulated in hot condition for 8 hrs and after 8 hrs it was filtered clear. The clear filtrate was passed from bottom of an adsorbent column comprising of Amberlite XAD-4 and the liquid out flow was monitored by thin layer chromatography using a mobile phase of petroleum ether:ethyl acetate in the ratio of 7:3. After achieving column saturation the column was washed with 60% methyl alcohol in water until no color.

The bed was eluted with pure ethyl alcohol at room temperature and the elutes were collected at the bottom. The eluted solvent was diluted with water to get the product in solution form in a 50% alcoholic solution. This was extracted with Toluene and the top toluene layer collected and Passed through 10 kg of Neutral alumina column and concentrated at 60° C. under vacuum. The resultant powder was analyzed by HPLC and was found to be 92% pure.

Example 4

256 gms of the 96% pterostilbene (of Example 1) was taken along with 2500 cc of ethyl alcohol. This solution was heated under agitation at 70° C. to get clear solution. To this solution an aqueous solution of sodium hydroxide comprising of 40 gms sodium hydroxide and 400 cc of water. This solution was refluxed for 2 hrs at 75° C. and to this 1.25 kg of β-cyclodextrin added and refluxed for further until it forms a clear solution This solution was agitated and cooled slowly and stirred at room temperature for 6 hrs and filtered. The filtered crystals were dried under vacuum for 6 hrs at 60° C. This was analyzed by HPLC and purity was found to be 15.3% Pterostilbene. This is water soluble and can be administered for testing.

Example 5

Deseeded frozen blueberry was pulped in a pulping machine. The paste was extracted with 60% ethyl alcohol in water at room temperature for 5 hrs and filtered clean of any fibers and rind pieces. The clear filtrate was subjected to the adsorbent column using Amberlite XAD-4 and washed thoroughly with 60% ethyl alcohol until the eluent is free of colors. The column is further subjected to pure alcoholic elution and the elute was diluted with water followed by filtration and dilution to achieve 50% alcohol content in the liquid. This liquid was subjected to counter current extraction with Toluene and finally subjected to neutral alumina column and concentrated and dried. This powder was analyzed for trans pterostilbene and contains 96%.

Example 6

*Pterocarpus santalinous* (raktha chandan) hardwood chips of 8 to 10 mm thickness were pulverized to 40 mesh powder in a hammer mill and packed in a vertical tubular extractor. The bottom of the extractor comprises of a perforated plate on which filtration cloth was fixed. The bottom of the extractor was connected to a receiver which in turn can be used as a reservoir for pumping the extract as well as circulation of the extract in the tube in counter current or concurrent manner.

The above mentioned mass was extracted with six bed volumes 60% volume by volume ethyl alcohol (aqueous) at 55° C. The bed was re extracted in manner with an extract collected at the bottom and re-circulated in hot condition for 8 hrs and after 8 hrs it was filtered clear. The clear filtrate was passed from bottom of an adsorbent column comprising of Amberlite XAD-4 and the liquid out flow was monitored by thin layer chromatography using a mobile phase of pet ether:ethyl acetate in the ratio of 7:3. After achieving column saturation the column was washed with 60% methyl alcohol in water until no color.

The bed was eluted with pure ethyl alcohol at room temperature and the elutes were collected at the bottom. The eluted solvent was diluted with water to get the product in solution form in a 50% alcoholic solution. This was extracted with Toluene and the top toluene layer collected and Passed through 10 kg of Neutral alumina column and concentrated at 60° C. under vacuum. The resultant powder was analyzed by HPLC and was found to be 94%.

Example 7

The Pterostilbene powder from Example 1 was dissolved in alcohol, preferably ethyl alcohol or isopropyl alcohol at a reflux temperature. To this one equivalent of a base preferably sodium hydroxide was added in aqueous solution and refluxed for a minimum of 2 hrs and can be extended up to 6 hrs at reflux temperature. To the above hot solution one equivalent of β-cyclodextrin was added slowly under agitation at reflux temperature.

The above mixture was further refluxed for 3 more hours and cooled under agitation. The above mixture was further stirred at room temperature for 3 hrs and filtered. The solids were collected and dried under vacuum at 60° C. for a minimum of 6 hrs to attain constant weight. The above material was powdered and analysed for pterostilbene content using HPLC.

Example 8

Commercially Scalable Process of Extraction of Pterostilebene 1000 kg of *Pterocarpus marsupium* hardwood was cut in to small pieces of 10 mm in length. These pieces were pulverized to 40 mesh powder in a hammer mill and stacked in a vertical tubular extractor. The bottom of the extractor comprises of a perforated plate on which filtration cloth was fixed. The bottom of the extractor was connected to a receiver which in turn can be used as a reservoir for pumping the extract as well as circulation of the extract in the tube in counter current or concurrent manner.

The above mentioned mass was extracted with six bed volumes of 60% volume by volume ethyl alcohol (aqueous) at 55° C. The bed was re-extracted in manner with an extract collected at the bottom and re-circulated in hot condition for 8 hrs and after 8 hrs it was filtered clear. The clear filtrate was passed from bottom of an adsorbent column comprising of 275 liters of Dowex L-493 or Its equivalent and the liquid out flow was monitored by thin layer chromatography using a mobile phase of petroleum ether:ethyl acetate in the ratio of 7:3. After achieving column saturation the column was washed with 60% ethyl alcohol in water until no color.

The bed was eluted with pure ethyl alcohol at room temperature and the elutes were collected at the bottom. The eluted solvent was diluted with water to get the product in solution form in a 50% alcoholic solution. This was extracted with Toluene 500 liters X3 times and the top toluene layer collected and passed through 100 kg of Neutral alumina column and concentrated at 60° C. under vacuum to get 5.3 kgs of powder off white in colour The resultant powder was analyzed by HPLC and was found to be 96%.

Example 9

Effect on SIRT1 and SIRT2 Enzymes (in Vitro): SIRT 1 and 2 Inhibition

Seven homologs (SIRT1-7) have been identified in the human genome. Despite their enzymatic activity on histone substrates in vitro, evidence suggests that SIRT proteins predominantly target non-histone proteins for deacetylation in both the nucleus and the cytoplasm.

Human histone deacetylase HDAC proteins are organized into classes based on their similarity to yeast HDAC proteins. Class III HDACs, also named sirtuins (SIRTs), are homologous to the yeast transcriptional repressor silent information regulator 2p (Sir2p).

This example evaluates the effect of the test compound on the SIRT 1 and 2 enzymes.

Human recombinant deacetylase sirtuin SIRT2 expressed in *E. coli* was used. Test compound (1, 10, 100 and 1000 µg/ml conc.) and/or vehicle was pre-incubated with 2 µg/ml enzyme in Tris-HCl buffer pH 8.0 for 15 minutes at 37° C. The reaction is initiated by addition of 25 µM Fluor de Lys-SIRT1 and 150 µM NAD for another 120 minute incubation period and is terminated by further addition of Fluor de Lys Developer. Determination of the amount of de-acetate Fluor de Lys formed is read spectrofluorimetrically with excitation at 360 nm and emission at 465 nm. The concentration-response (% inhibition) curve was plotted and $IC_{50}$ was calculated.

Figure 1:
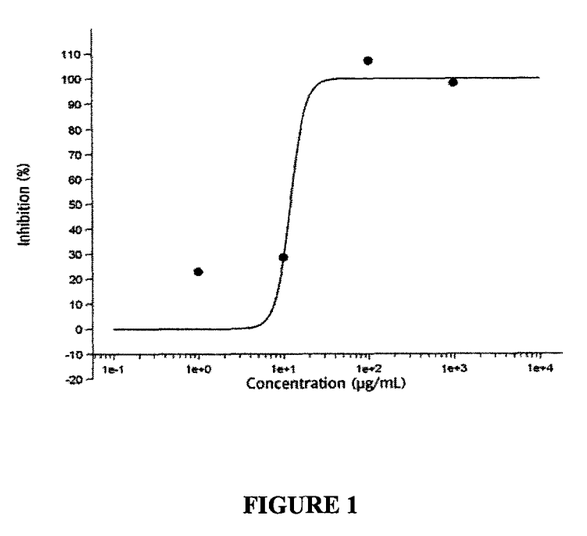
FIG. 1: Effect of pterostilbene on SIRT1 inhibition.
Figure 2:
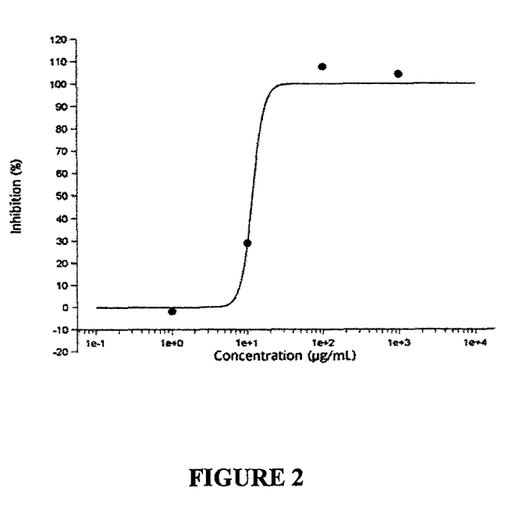
FIG. 2: Effect of pterostilbene on SIRT2 inhibition.

The results for this example are shown in the graph represented in FIG. 1 and FIG. 2 respectively.

IC50 for SIRT1 was found to be 12.1 µg/ml (i.e. 0.047 µM/mL)=47 nM/mL

IC50 for SIRT2 was found to be 11.7 µg/ml (i.e. 0.045 µM/mL)=45 nM/mL

Example 10

Effect on 3-NP Induced HD in Rats In Vivo

3-NP (3-Nitropropionic Acid) has been shown to cause symptoms of Huntington's disease in exposed rats. Administration of 3-nitropropionic acid, an inhibitor of the mitochondrial citric acid cycle, produces very selective striatal degeneration and results in a progressive locomotor deterioration in rodents resembling that of Huntington's disease.

3-NP (20 mg/kg i.p., daily in 2 divided doses) was administered to all the Wistar rats of weight range 250-300 g. in two divided doses at 12 hr interval for 9-11 days until disease is induced (acutely ill). It took 12 days to completely induce the disease symptoms. 3-NP was diluted with water and the pH will be adjusted upto 7.4 with NaOH. It was administered intraperitoneally (i.p.) at a dose of 10 mg/kg every 12 hrs (8:00 am and 8:00 pm) for 12 days (total daily dose 20 mg/kg). The observations were done on day 0, 7, 9, 11 and 13. The test compound was administered for the same period p.o. (per oral) one hour before 3-NP injection (at 7:00 AM daily) at dose of 30 mg/kg, p.o. The experimental groups were as follows: 1) Healthy Control: No treatment 2) HD control (3-NP+cyclodextrin) 3) TEST COMPOUND (30 mg/kg, p.o. daily complexed with cyclodextrin) treated.

The result of this example was evaluated based on the following parameters:

2) Body Weight

TABLE 1

Effect of Test Compound on % difference of body weights of rats after 3-NPA induced HD. (no. of animals in each group were 6)

| Day of Treatment | Healthy Control | Cyclo + 3-NPA | Test (30) + 3-NPA |
|---|---|---|---|
| Day 7 | 4.59 ± 2.82 | −5.37 ± 2.80 | 1.90 ± 3.72 |
| Day 9 | 2.74 ± 2.79 | −10.75 ± 2.96 | −0.82 ± 3.77 |
| Day 11 | 3.12 ± 2.83 | −12.48 ± 3.49 | −2.53 ± 3.70 |
| Day 13 | 3.64 ± 2.72 | −14.81 ± 3.15 | −6.08 ± 4.10 |

2) Neurological Problems

Behavioral changes were recorded daily, and immediately before sacrifice, graded according to the neurological scale described. A total of 6 grades included:
 Grade 0: normal behavior;
 Grade 1: general slowness in movement due to mild hind-limb impairment;
 Grade 2: prominent gait abnormality with poor coordination;
 Grade 3: nearly complete hind-limb paralysis;
 Grade 4: incapability to move due to four-limb impairment; and
 Grade 5: recumbence.

After 12-day treatment of 3-NPA (20 mg/kg, per day) treatment increased the neurological problems from 0 to 17 whereas the Test treatment restricted the problems to 13.

TEST COMPOUND could reduce neurological problems by 23.52% as compared to vehicle (cyclo+3-NPA) group. The results are given as reflected in Table 2 below.

TABLE 2

Effect of Test Compound on neurological behavioral changes after 3-NPA induced HD.

| Day of Treatment | Healthy control | Cyclo + 3-NPA | Test (30) + 3-NPA (% change from cyclo + 3-NPA treatment) |
|---|---|---|---|
| Day 7 | 0 | 6 | 0 |
| Day 9 | 0 | 6 | 1 (−83.33%) |
| Day 11 | 0 | 10 | 7 (−30%) |
| Day 13 | 0 | 17 | 13 (−23.52%) |

3) No of Squares Crossed in Open Field Test

Effect of Test compound on number of squares crossed in open field test of rats after 3-NPA induced HD

TABLE 3

Effect of Test compound on number of squares crossed in open field test of rats after 3-NPA induced HD

| Day of Treatment | Healthy control | Cyclo + 3-NPA | Test (30) + 3-NPA |
|---|---|---|---|
| Day 7 | 167.50 ± 10.93 | 146.83 ± 5.88 | 144.17 ± 7.47 |
| Day 9 | 170.33 ± 8.53 | 90.00 ± 6.74### | 125.67 ± 6.22* |
| Day 11 | 166.50 ± 12.74 | 63.67 ± 7.43### | 109.00 ± 13.72** |
| Day 13 | 158.33 ± 13.21 | 55.33 ± 7.68### | 77.83 ± 6.92* |

4) Brain Weight

Figure 3:
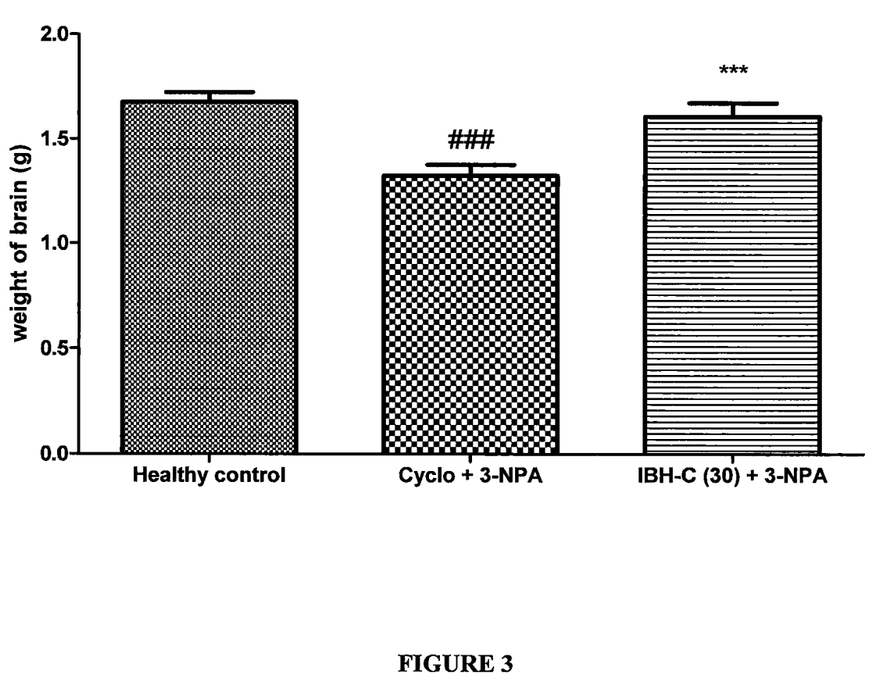
FIG. 3: Effect of test compound on mice brain weight.

On day 13, the brains of the rats were dissected out and cleaned. The wet weight of the brains were recorded for each rat. The results are also graphically represented in FIG. 3

TABLE 4

Effect of Test compound on Brain weight (g) of rats after 3-NPA induced HD

| Day of Treatment | Brain weight (g)-Mean ± SEM | | |
|---|---|---|---|
| | Healthy control | Cyclo + 3-NPA | Test (30) + 3-NPA |
| Day 13 | 1.675 ± 0.0472 | 1.323 ± 0.0521### | 1.605 ± 0.0659*** |

Based on the Example 10 it can be concluded that test compound significantly reverses the symptoms of 3-NP induced HD. After 11 days, 3-NP induces 12.48% reduction in body weight whereas test compound halts the body weight reduction and caused only a 2.53% reduction in body weight. Moreover, the neurological score (indicative of progression of HD) was significantly less (by 23.52%) in test compound group. Neuronal damage by 3-NP was reversed by the test compound, which is evident from significant increase in number of squares crossed in open field test.

Shrinkage of the brain is an important clinical parameter which can be seen after 3-NP induced HD in rats. 3-NP reduced weight of brain from 1.675 to 1.323 while the test compound reversed this weight loss of brain.

Example 11

100 kg of *Pterocarpus marsupium* hardwood was cut in to small pieces of 10 mm in length. These pieces were pulverized to 40 mesh powder in a hammer mill and stacked in a vertical tubular extractor. The bottom of the extractor comprises of a perforated plate on which filtration cloth was fixed. The bottom of the extractor was connected to a receiver which in turn can be used as a reservoir for pumping the extract as well as circulation of the extract in the tube in counter current or concurrent manner.

The above mentioned mass was extracted with six bed volumes of 60% volume by volume ethyl alcohol (aqueous) at 55° C. The bed was re-extracted in manner with an extract collected at the bottom and re-circulated in hot condition for 8 hrs and after 8 hrs it was filtered clear. The clear filtrate was passed from bottom of an adsorbent column comprising of Dowex L-493 and the liquid out flow was monitored by thin layer chromatography using a mobile phase of petroleum ether:ethyl acetate in the ratio of 7:3. After achieving column saturation the column was washed with 60% ethyl alcohol in water until no color.

The bed was eluted with pure ethyl alcohol at room temperature and the elutes were collected at the bottom. The eluted solvent was diluted with water to get the product in solution form in a 50% alcoholic solution. This was extracted with Toluene 50 liters X3 Times and the top toluene layer collected and Passed through 10 kg of Neutral alumina column and concentrated at 60° C. under vacuum. The resultant powder was analyzed by HPLC and was found to be 96% pure.

256 gms of the above purified pterostilbene was taken along with 2500 cc of ethyl alcohol. This solution was heated under agitation at 70° C. to get clear solution. To this solution an aqueous solution of sodium hydroxide comprising of 40 gms sodium hydroxide and 400 cc of water. This solution was refluxed for 2 hrs at 75° C. and to this 1.25 kg of β-cyclodextrin added and refluxed for further until it forms a clear solution This solution was agitated and cooled slowly and stirred at room temperature for 6 hrs and filtered. The filtered crystals were dried under vacuum for 6 hrs at 60° C. This was analyzed by HPLC and purity was found to be 15.3% Pterostilbene. This is water soluble and can be administered for testing.

Effect on SIRT1 and SIRT2 Enzymes (In Vitro): SIRT 1 and 2 Inhibition

Seven homologs (SIRT1-7) have been identified in the human genome. Despite their enzymatic activity on histone substrates in vitro, evidence suggests that SIRT proteins predominantly target non-histone proteins for deacetylation in both the nucleus and the cytoplasm.

Human histone deacetylase HDAC proteins are organized into classes based on their similarity to yeast HDAC proteins. Class III HDACs, also named sirtuins (SIRTs), are homologous to the yeast transcriptional repressor silent information regulator 2p (Sir2p).

This example thus evaluates the effect of the test compound on the SIRT 1 and 2 enzymes.

Human recombinant deacetylase sirtuin SIRT2 expressed in E. coli was used. Test compound (1, 10, 100 and 1000 μg/ml conc.) and/or vehicle was pre-incubated with 2 μg/ml enzyme in Tris-HCl buffer pH 8.0 for 15 minutes at 37°C. The reaction is initiated by addition of 25 μM Fluor de Lys-SIRT1 and 150 μM NAD for another 120 minute incubation period and is terminated by further addition of Fluor de Lys Developer. Determination of the amount of de-acetate Fluor de Lys formed is read spectrofluorimetrically with excitation at 360 nm and emission at 465 nm. The concentration-response (% inhibition) curve was plotted and $IC_{50}$ was calculated.

The results for this example are shown in the graph represented in FIG. 1 and FIG. 2 respectively.

IC50 for SIRT1 was found to be 12.1 μg/ml (i.e. 0.047 μM/mL)=47 nM/mL

IC50 for SIRT2 was found to be 11.7 μg/ml (i.e. 0.045 μM/mL)=45 nM/mL

Effect on 3-NP Induced HD in Rats In Vivo

3-NP (3-Nitropropionic Acid) has been shown to cause symptoms of Huntington's disease in exposed rats. Administration of 3-nitropropionic acid, an inhibitor of the mitochondrial citric acid cycle, produces very selective striatal degeneration and results in a progressive locomotor deterioration in rodents resembling that of Huntington's disease.

3-NP (20 mg/kg i.p., daily in 2 divided doses) was administered to all the Wistar rats of weight range 250-300 g. in two divided doses at 12 hr interval for 9-11 days until disease is induced (acutely ill). It took 12 days to completely induce the disease symptoms. 3-NP was diluted with water and the pH will be adjusted upto 7.4 with NaOH. It was administered intraperitoneally (i.p.) at a dose of 10 mg/kg every 12 hrs (8:00 am and 8:00 pm) for 12 days (total daily dose 20 mg/kg). The observations were done on day 0, 7, 9, 11 and 13. The test compound was administered for the same period p.o. (per oral) one hour before 3-NP injection (at 7:00 AM daily) at dose of 30 mg/kg, p.o. The experimental groups were as follows: 1) Healthy Control: No treatment 2) HD control (3-NP+cyclodextrin) 3) TEST COMPOUND (30 mg/kg, p.o. daily complexed with cyclodextrin) treated.

The result of this example was evaluated based on the following parameters:

1) Body Weight

Table 1 above indicates the effect of Test Compound on % difference of body weights of rats after 3-NPA induced HD. (no. of animals in each group were 6)

2) Neurological Problems

Behavioral changes were recorded daily, and immediately before sacrifice, graded according to the neurological scale described. A total of 6 grades included:

Grade 0: normal behavior;

Grade 1: general slowness in movement due to mild hind-limb impairment;

Grade 2: prominent gait abnormality with poor coordination;

Grade 3: nearly complete hind-limb paralysis;

Grade 4: incapability to move due to four-limb impairment; and

Grade 5: recumbence.

After 12-day treatment of 3-NPA (20 mg/kg, per day) treatment increased the neurological problems from 0 to 17 whereas the Test treatment restricted the problems to 13. TEST COMPOUND could reduce neurological problems by 23.52% as compared to vehicle (cyclo+3-NPA) group. The results are reflected in Table 2 above.

3) No of Squares Crossed in Open Field Test

The effect of Test compound on number of squares crossed in open field test of rats after 3-NPA induced HD are summarized in Table 3 above.

4) Brain Weight

On day 13, the brains of the rats were dissected out and cleaned. The wet weight of the brains were recorded for each rat. The results are also graphically represented in FIG. 3 Table 4 above shows the effect of Test compound on Brain weight (g) of rats after 3-NPA induced HD Based on the Example 10 it can be concluded that test compound significantly reverses the symptoms of 3-NP induced HD. After 11 days, 3-NP induces 12.48% reduction in body weight whereas test compound halts the body weight reduction and caused only a 2.53% reduction in body weight. Moreover, the neurological score (indicative of progression of HD) was significantly less (by 23.52%) in test compound group. Neuronal damage by 3-NP was reversed by the test compound, which is evident from significant increase in number of squares crossed in open field test.

Shrinkage of the brain is an important clinical parameter which can be seen after 3-NP induced HD in rats. 3-NP reduced weight of brain from 1.675 to 1.323 while the test compound reversed this weight loss of brain.

Examples 9, 10 and 11, in combination show the therapeutic effect of the test drug for the treatment of CNS diseases in specific Huntington's Disease. Specifically the in vitro studies on SIRT2 inhibition, shows that the test compound is a SIRT2 inhibitor. SIRT2 is a Class III HDAC. As described earlier HDAC inhibitors have an array of pharmacologically activities specifically in Polyglutamine-Repeat disorders. Thus, the test compound, in addition to being useful specifically in HD, has therapeutic activity in other polyglutamine repeat disorders.

We claim:

1. A process of obtaining purified Pterostilbene having purity of about 99% from a botanical source selected from the group consisting of *Pterocarpus* genus, *Anogeissus* genus, Vitaceae family and Vaccinium family, said process comprising steps:
    a) pulverizing and extracting of the botanical source with about 60% v/v of isopropyl alcohol to obtain an extract;
    b) filtering the extract and subjecting the extract to an adsorbent column, wherein a column outflow is monitored by thin layer chromatography using a mobile phase of petroleum ether:ethyl acetate in a ratio of 7:3; and
    c) washing the adsorbent column with about 60% v/v of isopropyl alcohol in water and eluting the extract within the adsorption column with ethyl alcohol, followed by extracting with toluene and passing through a neutral alumina column for concentration under vacuum to obtain the purified pterostilbene.

2. The process of claim 1, wherein the pulverizing is conducted to a mesh size of about 40 mesh to 60 mesh to obtain pulverized material; and wherein the pulverized material is extracted at a temperature range of about 50° C. to 60° C. for a duration of about 8 to 12 hrs to obtain the extract.

3. The process of claim 1, wherein the extract, is filtered through a clean stainless steel mesh or a clean cloth.

4. The process of claim 1, wherein the extracted extract is concentrated at a temperature range of about 40° C. to 60° C. under vacuum.

5. The process of claim 1, further comprising complexing pterostilbene with a carrier; wherein the carrier is a cyclodextrin selected from the group consisting of α-cyclodextrin, β-cyclodextrin and γ-cyclodextrin.

6. Purified pterostilbene having purity of about 99%, wherein the pterostilbene is obtained from a botanical source selected from the group consisting of *Pterocarpus* genus, *Anogeissus* genus, Vitaceae family and Vaccinium family, wherein the purified pterostilbene is obtained by a process comprising steps:
    a) pulverizing and extracting of the botanical source with about 60% v/v of isopropyl alcohol to obtain an extract;
    b) filtering the extract and subjecting the extract to an adsorbent column, wherein a column outflow is monitored by thin layer chromatography using a mobile phase of petroleum ether:ethyl acetate in a ratio of 7:3; and
    c) washing the adsorbent column with about 60% v/v of isopropyl alcohol in water and eluting the extract within the adsorption column with ethyl alcohol, followed by extracting with toluene and passing through a neutral alumina column for concentration under vacuum to obtain the purified pterostilbene.

7. A process for inhibition of Histone Deacetylases using pterostilbene complexed with cyclodextrin, said process comprising step of contacting the histone deacetylase with the purified pterostilbene of claim 6.

8. The process of claim 7, wherein the Histone Deacetylase is SIRT1 or SIRT2.

9. The process of claim 7, wherein the pterostilbene inhibits Histone Deacetylases; and wherein the cyclodextrin is selected from the group consisting of α-cyclodextrin, β-cyclodextrin and γ-cyclodextrin.

10. A method of managing Poly Glutamine repeat disorder, said method comprising step of administering a therapeutically effective amount of the purified pterostilbene of claim 6 complexed with cyclodextrin to a subject in need thereof.

11. The method of claim 10, wherein the Poly Glutamine Repeat disorder is Huntington's disease; and wherein the poly Glutamine repeat disorder is selected from the group consisting of Spinocerebellar ataxias (SCAs) 1, Spinocerebellar ataxias (SCAs) 2, Spinocerebellar ataxias (SCAs) 3, Spinocerebellar ataxias (SCAs) 6, Spinocerebellar ataxias (SCAs) 7, Spinocerebellar ataxias (SCAs) 17, Spinal and bulbar muscular atrophy (SBMA) and Dentatorubropallidoluysian atrophy (DRPLA).

12. The method of claim 10 wherein the pterostilbene inhibits Histone Deacetylases for managing Poly Glutamine repeat disorder; and wherein the cyclodextrin is selected from the group consisting of α-cyclodextrin, β-cyclodextrin and γ-cyclodextrin.

13. The method of claim 12, wherein the Histone Deacetylase is SIRT1 or SIRT2.

14. The method of claim 10, wherein the therapeutically effective amount of pterostilbene ranges from about 2 mg/kg to 20 mg/kg body weight of the subject and wherein the subject is animal or human.

15. Purified pterostilbene having purity of about 96% to 99%, wherein the pterostilbene is obtained from a botanical source selected from the group consisting of *Pterocarpus* genus, *Anogeissus* genus, Vitaceae family and Vaccinium family, wherein the purified pterostilbene is obtained by a process comprising steps:
    a) pulverizing and extracting of the botanical source with about 60% v/v of isopropyl alcohol or ethyl alcohol to obtain an extract;
    b) filtering the extract and subjecting the extract to an adsorbent column, wherein a column outflow is monitored by thin layer chromatography using a mobile phase of petroleum ether:ethyl acetate in a ratio of 7:3; and
    c) washing the adsorbent column with about 60% v/v of isopropyl alcohol or ethyl alcohol in water and eluting the extract within the adsorption column with ethyl alcohol, followed by extracting with toluene and passing through a neutral alumina column for concentration under vacuum to obtain the purified pterostilbene.

* * * * *